United States Patent [19]

Hesse et al.

[11] Patent Number: Plant 5,443

[45] Date of Patent: Apr. 23, 1985

[54] KALANCHOE PLANT NAMED SONORA

[75] Inventors: Peter S. Hesse, Bradenton, Fla.; Margaret M. Fleming, Half Moon Bay, Calif.

[73] Assignee: Pan American Plant Company, Parrish, Fla.

[21] Appl. No.: 510,409

[22] Filed: Jul. 1, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinctive Kalanchoe plant named Sonora, characterized by rose colored flowers, compact habit, highly floriferous habit, free branching, average 15-week flowering response, and its adaptability to production in 10–15 cm. pots.

1 Drawing Figure

The present invention relates to a new and distinctive cultivar of Kalanchoe plant, botanically known as Kalanchoe, and referred to by the cultivar name Sonora.

The new cultivar was referred to during the breeding selection process by the designation K78-117-R, and is a product of a planned breeding program. The basic objective of the breeding program was to create a new Kalanchoe cultivar having rose colored flower petals, compact habit, and the ability to produce commercially acceptable quality in a year-round Kalanchoe program.

The new cultivar was originated from a cross made by a technician working under the supervision of Margaret M. Fleming in a controlled breeding program at West Chicago, Ill. The male and female parents are unknown at this time.

Sonora was discovered and selected by Peter S. Hesse as a flowering plant within the progeny of the stated cross in a controlled environment in West Chicago, Ill. Asexual reproduction of the new cultivar by stem cuttings, as performed at West Chicago, Ill. and Parrish, Fla., has demonstrated that the combination of characteristics as herein disclosed for the new cultivar are firmly fixed and are retained through successive generations of asexual reproduction.

Sonora has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Sonora, which in combination distinguish this Kalanchoe as a new and distinct cultivar:

(1) Rose colored flowers.

(2) Compact habit; slow growth rate as compared to other commercial Kalanchoe cultivars.

(3) Freely branching, with shoots formed at every node.

(4) Suitable for production in 10 to 15 cm. pots.

(5) Flowering in 13 weeks under favorable conditions and up to 16 weeks under less favorable conditions.

(6) Highly floriferous, with numerous flowers formed at every shoot.

(7) To reduce peduncle elongation after flower initiation, plants can be treated with B-9.

The new cultivar is most similar to Regulus, disclosed in U.S. Plant Pat. No. 4,817. Sonora is principally distinguished from Regulus by its rose colored flowers and its one week later flowering response.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S), except where general colors of ordinary signficance are referred to. Color values are taken under natural light conditions in Parrish, Fla.

BOTANICAL CLASSIFICATION

Kalanchoe, cv. SONORA.

PROPAGATION

The new cultivar holds its distinguishing characteristics through successive propagations by leaf cuttings and by division of shoots.

Type cutting: Tip cuttings, with stems up to 2 cm. long.

Time to root: 10 days at 21° C. summer, 14 days at 21° C. winter.

Rooting habit: Fibrous, many very fine roots.

PLANT DESCRIPTION

A. Form: Upright, short, compact. Growing and scheduling practices can produce small plants in 10 cm. pots or large plants in 15 cm. pots.

B. Habit of growth: Slow growth rate for this type of plant. Shoots are normally formed at every node.

C. Foliage description: Leaves simple, opposite, generally symmetrical.

(1) *Size.*—Average full grown leaf of a flowering plant in a 10 cm. pot is 80–110 cm. long and 65–90 wide. Plants in larger pots have proportionately larger full leaves.

(2) *Shape.*—Ovate, apex obtuse, base acute.

(3) *Texture.*—Glabrous, coriaceous, succulent.

(4) *Margin.*—Crenate.

(5) *Color.*—Young foliage top side, 147A, under side, 147B. Mature foliage top side, 147A, under side 147B.

FLOWERING DESCRIPTION

Flowering habit: Inflorescence of each shoot is formed by dichotomous branching, starting with opening of terminal flowers of the side branches of the inflorescence. Opening of new buds will continue for 2 months or more. Individual flowers last two weeks or more after opening.

Natural flowering season is January. Flowering time under controlled day length at 30° C. in summer is 16 weeks; in spring and fall at 25° C., 13 weeks. Flowering time depends on temperature, light intensity and other growing conditions.

Flower buds: Oblong, developing to tubular as petals mature, sheathed with four green sepals; corolla at maturity about 14 mm. long.

(1) *Size.*—Up to 15 mm. long.

(2) *Shape.*—Oblong.

(3) *Rate of opening.*—Normal.

Flowers borne: Compound dichasial cyme on strong peduncles. Peduncle length depends on growing conditions and B-9 applications. Pedicles up to 5 mm. long.

Quantity of flowers: Very floriferous, with new buds continuing to develop.

Petals:

(1) *Shape.*—Nearly round, apex cuspidate.

(2) *Color.*—Top side when opening, 43A, fading to 34A; under side, 20D.

(3) *Number and size of petals.*—Four; united in corolla 7 mm. in diameter; total flower diameter 15 mm.

Reproductive organs:

(1) *Stamens.*—8 In number. (a) Anther shape: Flat, elliptical. (b) Filament color: Yellow. (c) Pollen color: Yellow.

(2) *Pistels.*—(a) Stigma shape: Flat, crystalline. (b) Style color: Greenish-white. (c) Ovaries: 4 celled, 7 mm. long, green.

DISEASE RESISTANCE

No known Kalanchoe diseases observed to date.

We claim:

1. A new and distinctive Kalanchoe plant named Sonora, as described and illustrated, and particularly characterized by rose colored flowers, compact habit, highly floriferous habit, free branching, average 15-week flowering response, and its adaptability to production in 10–15 cm. pots.

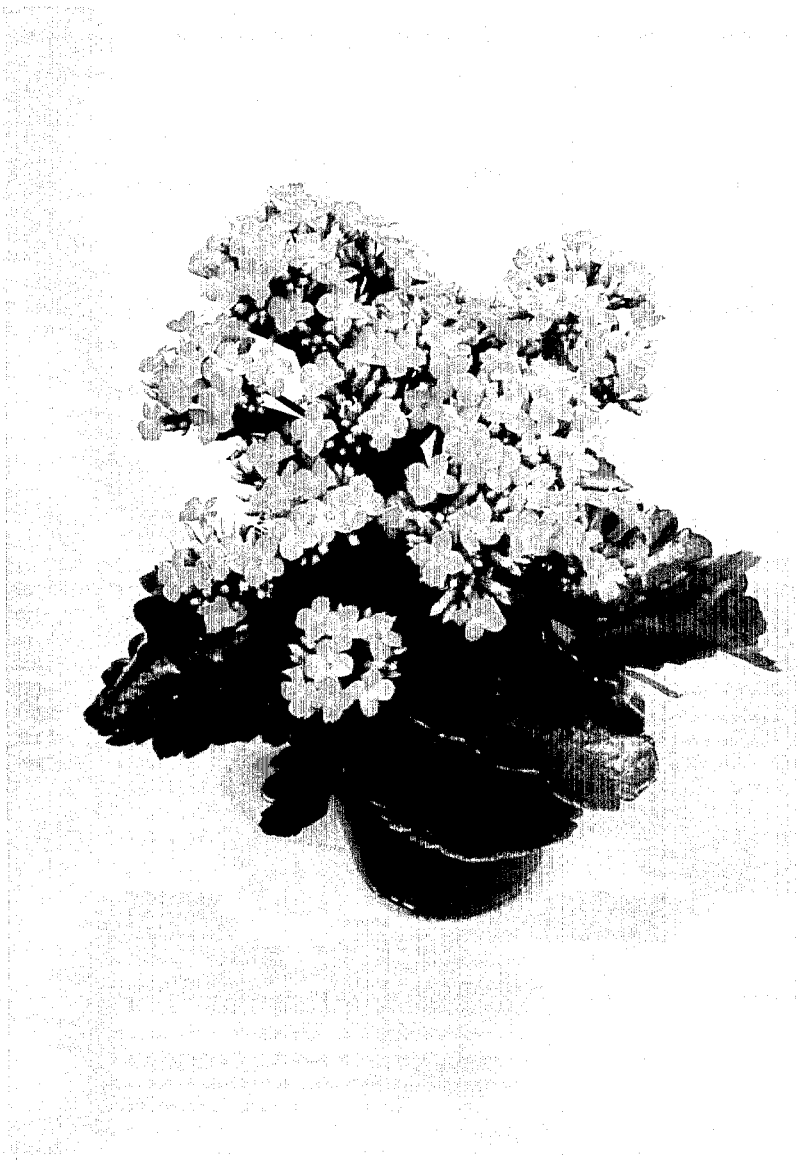

* * * * *